United States Patent [19]
Liversidge et al.

[11] Patent Number: 5,628,981
[45] Date of Patent: May 13, 1997

[54] FORMULATIONS OF ORAL GASTROINTESTINAL DIAGNOSTIC X-RAY CONTRAST AGENTS AND ORAL GASTROINTESTINAL THERAPEUTIC AGENTS

[75] Inventors: Gary Liversidge, West Chester; W. Mark Eickhoff, Downingtown; Kathleen J. Illig, Phoenixville; Pramod Sarpotdar, Malvern; Stephen B. Ruddy, Schwenksville, all of Pa.

[73] Assignee: Nano Systems L.L.C., Collegeville, Pa.

[21] Appl. No.: 366,841

[22] Filed: Dec. 30, 1994

[51] Int. Cl.⁶ .................................................. A61K 49/04
[52] U.S. Cl. .................... 424/94; 424/9.45; 514/461; 514/975
[58] Field of Search ........................ 424/9.4, 9.45; 514/54, 57, 461, 975

[56] References Cited

U.S. PATENT DOCUMENTS

| | | | |
|---|---|---|---|
| 4,107,288 | 8/1978 | Oppenheim et al. | 424/22 |
| 4,501,726 | 2/1985 | Schroder et al. | 424/1.1 |
| 5,015,452 | 5/1991 | Matijevic | 423/263 |
| 5,118,528 | 6/1992 | Fessi et al. | 427/213.36 |
| 5,145,684 | 9/1992 | Liversidge et al. | 424/489 |
| 5,310,538 | 5/1994 | Bacon et al. | 424/5 |
| 5,312,616 | 5/1994 | Illig et al. | 424/5 |
| 5,318,768 | 6/1994 | Illig et al. | 424/5 |
| 5,326,552 | 7/1994 | Na et al. | 424/4 |
| 5,326,553 | 7/1994 | Illig et al. | 424/5 |
| 5,336,484 | 8/1994 | Bacon et al. | 424/5 |
| 5,340,564 | 8/1994 | Illig et al. | 424/5 |
| 5,342,605 | 8/1994 | Illig | 424/5 |

*Primary Examiner*—Gary E. Hollinden
*Attorney, Agent, or Firm*—Rudman & Balogh

[57] ABSTRACT

Nanoparticulate crystalline x-ray contrast agents are formulated with stabilizers to enhance contact between the crystalline x-ray contrast agents and the gastrointestinal tract.

Nanoparticulate crystalline therapeutic substances also formulated with stabilizers to enhance contact between the crystalline therapeutic substances and the gastrointestinal tract and to provide extended therapeutic effect.

10 Claims, No Drawings

FORMULATIONS OF ORAL GASTROINTESTINAL DIAGNOSTIC X-RAY CONTRAST AGENTS AND ORAL GASTROINTESTINAL THERAPEUTIC AGENTS

BACKGROUND OF THE INVENTION

1. Field of the Invention

This invention relates to x-ray diagnostic imagining contrast formulations for imaging the gastrointestinal (hereinafter sometimes referred to as GI) tract. The formulations described herein have enhanced utility as oral/rectal GI diagnostic contrast agents.

This invention also relates to improved formulations of gastrointestinal therapeutic agents.

2. Reported Developments

It is a common medical practice to employ barium sulfate formulations to image the gastrointestinal tract of patients. Barium sulfate can be given either orally to visualize the stomach and upper GI tract or rectally to visualize the colon and lower GI tract. Barium sulfate is usually administered as a suspension that has limited stability even with the addition of stabilizers, it is often too opaque to visualize all segments of the GI tract, it often forms clumps that yield resultant radiopaque areas on x-ray films and has poor patient acceptability characteristics. Poor patient acceptability characteristics include palatability, patient discomfort during and after administration and constipation of the patient. Barium sulfate also shows poor affinity for coating the GI mucosa and consequently the patient is often needed to be manipulated or even rotated to ensure that the barium sulfate suspension coats the gastric mucosa. Nevertheless, segments of the GI tract are often either obscured or are not adequately coated to be visualized. It is not uncommon for the patient to undergo repeated examinations to achieve satisfactory imagining results.

The most serious failings of currently available formulations of barium sulfate are that they do not adequately coat the entire GI tract, requiring subsequent examination, and they pose safety concerns especially with patients that are suspected of having intestinal perforations or obstructions. Perforations of the upper GI tract or small bowel occurs with sufficient frequency that the risk of localized tissue injury is present. It is also not uncommon for orally administered barium sulfate to accumulate proximally to an obstruction in the bowel causing impaction that can lead to eventual perforation of the GI tract. In addition, aspiration of barium sulfate in the lungs may cause occlusion of the bronchioli and resultant pulmonary sequela.

Aqueous barium sulfate formulations are less constipating than non-aqueous barium sulfate formulations, however, they are often hypertonic, and consequently are irritating to the gastric mucosa.

Another class of compounds that have been investigated for imaging the GI tract are oil based emulsions of iodinated organic substances. Emulsions that have particle sizes of <0.3 microns have been reported to image the small intestines of dogs but 50–70% of the oil based emulsions are reported to be absorbed from the intestine. Oily emulsions also appear to coat to some extent both the upper and lower segments of the GI tract as compared with non-oil based contrast agents. Oily emulsions are not usually contraindicated for patients with intestinal perforations or with intestinal obstructions. The major problems associated with these oil based emulsions is their tendency to be absorbed from the GI tract and the inherent toxicity that may be associated with the absorption of these agents. Emulsions such as PANTOPAQUE, i.e., ethyl iodophenylundecylate, adhere to the gastric mucosa, have low viscosity, low surface tension, are miscible with tissue fluids and exhibit good radiopacity. However, the emulsions of these organic iodinated substances suffer from their undesirable toxic effects.

Accordingly, there is a need to provide oral GI diagnostic x-ray contrast agents that enable the visualization of both the upper and lower GI tract following a single administration, that is safe and efficacious and is not contraindicated for GI tract perforations and/or obstructions. Such an agent should have excellent mucosal coating properties for both the upper and lower GI tract, i.e. it should have mucoadhesive or bioadhesive properties that enable the entire GI tract to be visualized. The object of the present invention is to provide a formulation that enhances the imaging of the GI tract that takes into consideration the physical-chemical properties of the imaging agents, surface stabilizers and viscosity modifiers. There is a need to provide in such a formulation primary surface stabilizers with appropriate mucoadhesive properties and secondary excipients that provide for a marked improvement in imaging quality as compared with existing products and formulations. The identification of surface active stabilizers with bioadhesive or mucoadhesive properties that enable the imaging of the entire GI tract has not been reported to date. This represents a difficult technical problem that requires the application of mucoadhesive technology to develop appropriate surface active agents that will enable the entire GI tract to be visualized. Bioadhesion is usually achieved by interaction of either a synthetic or natural polymeric substance with the mucosal membranes of the GI tract. Such technology has been employed to enhance drug delivery by decreasing the transit time of a drug substance in the GI tract and hence promote an opportunity for enhanced absorption. With regards to the development of safe and effective x-ray contrast agents for visualizing the GI tract, it is important to identify mucosal adhesives that coat the GI surfaces and visualize diseased or abnormal tissues. Highly charged carboxylated polyanions are good candidates for use as bioadhesives in the GI tract. See, for example: Park, K. and Robinson, J. R., Bioadhesion: Polymers and Platforms for Oral-Controlled Drug Delivery; Method to Study Bioadhesion. Int. J. Pharm., 19, 107 (1984). The formation of a bioadhesive bond between a polymeric substance and the mucosal lining of the GI tract can be visualized as a two step process, i.e., initial contact between the two surfaces and the formation of secondary bonds due to non-covalent interactions. Bioadhesives specific for the GI tract must interact with the mucus layer during attachment. Mucus, a general term for the heterogenous secretion found on the epithelial surfaces of the GI tract, is made of the following components: glycoprotein macromolecules, inorganic salts, proteins, lipids and mucopolysaccharides. These glycoproteins typically consist of a protein core with carbohydrate side chains. This forms a network of mucus that is a continuous layer covering the GI tract. From a bioadhesive perspective, mucus consists of highly hydrated, crosslinked linear, flexible yet random coiled glycoprotein molecules with a net negative charge. Understanding the principles of bioadhesion is the basis for formulating an oral contrast x-ray agent for GI tract visualization. Bioadhesion accounts for the interaction between a biological surface and a biomaterial substance. As noted previously, bioadhesive agents are usually polymeric substances that adhere to tissues by ionic or covalent bonds or by physical attachment. Several theories of bioadhesion have been published including electronic, adsorption, wetting, diffusion and fracture theories. Bioadhesives bind to membrane surfaces and are retained for variable periods of time.

Crystalline x-ray contrast agents do not inherently adhere to the mucosal surfaces of the GI tract. It has now been discovered that crystalline x-ray contrast agents modified by the addition of surfactants, however, can be rendered so that they adsorb onto the GI mucosal surface. This is achieved by the use of mucoadhesive surfactants. The primary difficulty with previously reported mucoadhesive surfactants is that they do not interact effectively with both the particles and GI tract uniformly so that both the upper and lower GI tract can be visualized by a single agent during one examination. The surfactants used for this purpose must adsorb sufficiently to the different regions of the GI tract to enhance visualization by the contrast agent. In practice, surfactants tend to be adsorbed at some biological surfaces differentially than at others due to a variety of complex reasons. There is a need for contrast agents that are adsorbed sufficiently over the entire GI tract to allow adequate and uniform visualization of the different regions of the GI tract.

In accordance with the invention there is further provided a method for x-ray diagnostic imaging of the GI tract which comprises orally or rectally administering to the patient an effective amount contrast producing amount of the above-described x-ray contrast compositions.

A method for diagnostic imagining of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

In another embodiment the present invention relates to improved formulations of gastrointestinal therapeutic agents. These formulations possess the benefit of providing prolonged local contact of the therapeutic agents with the mucosal layer of the gastrointestinal tract.

SUMMARY OF THE INVENTION

In accordance with the present invention there is provided an orally/rectally administrable gastrointestinal diagnostic x-ray contrast formulation comprising:

of from about 4 to about 45% w/v, and preferably of from about 15 to about 25% w/v, of an essentially water insoluble or poorly water-soluble particulate radiopaque crystalline material having an effective average particle size of less than about 2,000 nm, more preferably an effective average particle size of less than about 1,000 nm, and most preferably an effective average particle size of less than about 400 nm;

of from about 0.5 to about 10% w/v, and preferably of from about 2 to about 6% w/v of a bioadhesive or mucoadhesive surfactant stabilizer (hereinafter sometimes referred to as "primary stabilizer"); and water to make 100% w/v.

Secondary stabilizers may also be used in the x-ray contrast formulation up to about 1% w/v, preferably up to about 0.2% w/v, and most preferably up to about 0.1% w/v. Secondary stabilizers include dioctylsulfosuccinate (DOSS) and sodium lauryl sulfate (SLS).

Other ingredients customarily used in oral pharmaceutical formulations may also be included, such as flavorants, colorants and preservatives to provide pharmaceutically acceptable and palatable formulations without such additional ingredients affecting the gastrointestinal imaging efficacy of the formulations.

The particulate radiopaque material used in the present invention includes: barium salts and crystalline organic compounds known for use in diagnostic imaging formulations.

The surfactants found to have bioadhesive or mucoadhesive properties include:

1) Poloxamers having an average molecular weight of from about 1,000 to 15,000 daltons;
2) Polyvinyl alcohol;
3) Polyvinyl pyrrolidone,
4) Hydroxypropyl methylcellulose; and
5) Polyoxyethylene sorbitan mono-oleate (Tween 80).

Poloxamers are polyethylene-polypropylene glycol block polymers containing ethylene oxide (PEO) and propylene oxide (PPO) moles according to the formula (PEO)a–(PPO)b–(PEO)c wherein a is 46, 52, 62, 75, 97, 98, 122 and 128;
b is 16, 30, 35, 39, 47, 54 and 67; and
c is 46, 52, 62, 75, 97, 98, 122 and 128.

Table 1 shows the various poloxamers by manufacturer-designated number.

TABLE 1

Molecular Weights of Poloxamers

| Poloxamer No. | Pluronic | Av. Mol. Wt. | Av. Values a | b | c |
|---|---|---|---|---|---|
| 401 | | 4,400 | 6 | 67 | 6 |
| 402 | | 5,000 | 13 | 67 | 13 |
| 403 | | 5,750 | 21 | 67 | 21 |
| 407 | F127 | 12,000 | 98 | 67 | 98 |
| 331 | | 3,800 | 7 | 54 | 7 |
| 333 | | 4,950 | 20 | 54 | 20 |
| 334 | | 5,850 | 31 | 54 | 31 |
| 335 | | 6,000 | 38 | 54 | 38 |
| 338 | F108 | 15,000 | 128 | 54 | 128 |
| 282 | | 3,650 | 10 | 47 | 10 |
| 284 | | 4,600 | 21 | 47 | 21 |
| 288 | F98 | 13,500 | 122 | 47 | 122 |
| 231 | | 2,750 | 6 | 39 | 6 |
| 234 | | 4,200 | 22 | 39 | 22 |
| 235 | | 4,600 | 27 | 39 | 27 |
| 237 | F87 | 7,700 | 62 | 39 | 62 |
| 238 | F88 | 10,800 | 97 | 39 | 97 |
| 212 | | 2,750 | 8 | 35 | 8 |
| 215 | | 4,150 | 24 | 35 | 24 |
| 217 | F77 | 6,600 | 52 | 35 | 52 |
| 181 | | 2,000 | 3 | 30 | 3 |
| 182 | | 2,500 | 8 | 30 | 8 |
| 183 | | 2,650 | 10 | 30 | 10 |
| 184 | | 2,900 | 13 | 30 | 13 |
| 185 | | 3,400 | 19 | 30 | 19 |
| 188 | F68 | 8,350 | 75 | 30 | 75 |
| 122 | | 1,630 | 5 | 21 | 5 |
| 123 | | 1,850 | 7 | 21 | 7 |
| 124 | | 2,200 | 11 | 21 | 11 |
| 101 | | 1,100 | 2 | 16 | 2 |
| 105 | | 1,900 | 11 | 16 | 11 |
| 108 | F38 | 5,000 | 46 | 16 | 46 |

Certain number of these surfactants are also known as Pluronic, which is a brand name of BASF Corporation.

Preferred surfactants for use in the present invention are:
Pluronic F127
Pluronic F108
Pluronic F98

Pluronic F87
Pluronic F88
Pluronic 77
Pluronic F68 and
Pluronic F38.

In another embodiment of the invention, there is provided an orally/rectally administrable therapeutic composition comprising:

of from about 0.1% to about 45% w/v, and preferably of from about 5% to about 25% w/v, of an essentially water insoluble or poorly water-soluble particulate crystalline material having an effective average particle size of less than about 2,000 nm, more preferably an effective average particle size of less than about 1,000 nm, and most preferably an effective average particle size of less than about 400 nm;

of from about 0.1% to about 10% w/v, and preferably of from about 1% to about 6% w/v of a bioadhesive or mucoadhesive surfactant stabilizer (hereinafter sometimes referred to as "primary stabilizer"); and water to make 100% w/v.

Secondary stabilizers may also be used in the therapeutic composition up to about 1% w/v, preferably up to about 0.2% w/v, and most preferably up to about 0.1% w/v. Secondary stabilizers include dioctylsulfosuccinate (DOSS) and sodium lauryl sulfate (SLS).

Other ingredients customarily used in oral pharmaceutical formulations may also be included, such as flavorants, colorants and preservatives to provide pharmaceutically acceptable and palatable formulations.

DETAILED DESCRIPTION OF THE INVENTION

The present invention is based on the discovery that particulate crystalline materials can be rendered mucoadhesive or bioadhesive in the gastrointestinal tract when the particulate crystalline material is combined with certain surface active agents in a suspension.

The invention can be practiced with a wide variety of crystalline materials that are water-insoluble or poorly soluble in water. As used herein "poorly soluble" means that the material has a solubility in aqueous medium of less than about 10 mg/ml, and preferably of less than about 1 mg/ml. Examples of preferred crystalline materials follow.

Drugs

Suitable drug substance can be selected from a variety of known classes of drugs including, for example, antacids, anti-inflammatory agents, antibiotics (including penicillins), antimycobacterial agents, antiviral agents, corticosteroids, parasympathomimetics, radio-pharmaceuticals, sympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants. Preferred drug substances include those intended for oral administration and rectal administration. A description of these classes of drugs and a listing of species within each class can be found in Martindale, The Extra Pharmacopoeia, Twenty-Ninth Edition, The Pharmaceutical Press, London, 1989, the disclosure of which is hereby incorporated by reference in its entirety. The drug substances are commercially available and/or can be prepared by techniques known in the art.

Radiopaque Materials

A preferred x-ray contrast agent utilized in the present invention is barium sulfate which is a white, radiopaque, crystalline powder that is essentially insoluble in water. It is commercially available in the particle size range of 0.001 to 0.1 micron diameter. Smaller particle size may also be obtained with techniques known in the prior art such as described in U.S. Pat. No. 5,145,684 which is incorporated herein by reference, or analogously, as described herein with respect to other crystalline radiopaque compounds. However, good results are obtainable with other finely-divided, inorganic, essentially water-insoluble salts of barium including barium hexaboride, barium chromite, barium fluogallate, barium tri-ortho phosphate, barium metasilicate, barium titanate and barium zirconate.

Preferred organic radiopaque crystalline compounds of the present invention include, but are not limited to the following compounds.

EXAMPLE 1

3,5-Bis-acetylamino-2,4,6-triiodo-benzoic acid ethyl ester (WIN 59316)

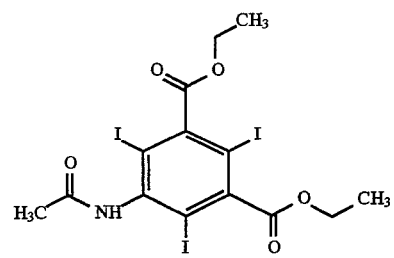

Molecular Wt.: 657
Melting Point: 219°–220° C.

EXAMPLE 2

2-(3,5-Bis-acetylamino-2,4,6-triiodo-benzyloxy)-2-methyl malonic acid(WIN 67975)

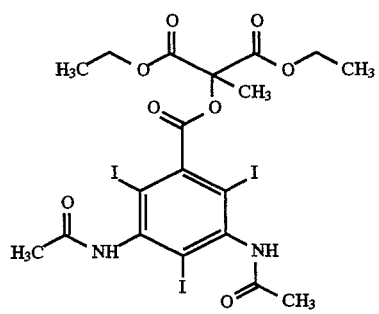

Preparation of WIN 67975 (described in U.S. Pat. No. 5,264,610)

A solution of sodium hypaque (50 g, 79 mmole) in 150 ml of dry DMF was treated with 16.6 ml (87 mmole) of diethyl 2-bromo-2-methylmalonate and the reaction mixture was heated for 12 hrs on a steam bath. After cooling, the solution was added to ice water and the resulting precipitate was collected by filtration, rinsed with water, ethyl acetate and dried under vacuum. The product was recrystallized from DMF-water to give 48.4 g (69%) of pure material, mp 268°–269° C. (dec.); CI-MS: MH+787. The $^1$H-NMR (300 MHz) spectral data was consistent with the desired material. Calculated for $C_{19}H_{21}I_3N_2O_8$: C 29.03, H 2.69, N 3.56, I 48.43; Found C 28.82, H 2.56, N 3.57, I 48.83.

EXAMPLE 3

Propanedioic Acid, [[3,5-bis-(acetylamino)-2,4,6-triiodo-benzoyl]oxy]-bis(1-methylethyl) ester (WIN 68165)

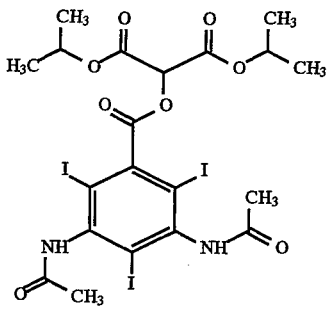

Molecular Wt.: 800.12
Melting Point: 252°–253° C.

EXAMPLE 4

Diethyl 5-acetylamino-2,4,6-triiodo-isophthalate (WIN 59316)

3.91 g (0.17 mol) of sodium was dissolved in 500 ml of ethanol. Then, 50 g (0.083 mol) of 5-acetylamino-2,4,6-triiodo-isophthalic acid was added and the solution was stirred for half hour. The solvent was stripped to yield an intermediate, disodium 5-acetylamino-2,4,6-triiodoisophthalate. 250 ml of dry N,N-dimethylformamide was added. The contents did not dissolve completely. 15 ml (29.2 g, 0.187 mol) of ethyl iodide was added and the solution was heated on stem bath for 2 hrs. The solution was poured into 4 liters of water, filtered and rinsed with cold water. Solid was dried in a vacuum oven over the weekend. Yield—52.18 g. MS results, MW=657 a.m.u. This product and 5.0 g prepared using a small scale identical procedure was combined, total weight—57.2 g. It was dissolved in 120 ml of N,N-dimethylformamide. The solution was filtered into 2 liters of filtered and distilled water. The contents were swirled by hand. White solid was filtered and dried at 110° C., 0.2 mm Hg for 20 hrs. Recovered 56.27 g, melting point, 219°–220° C., MS results, MW=656.98 a.m.u.

Elemental analysis: Calculated for $C_{14}H_{14}I_3NO_5$: C 25.54, H 2.15, N 2.13, I 57.95. Found C 25.80, H 2.06, N 1.99, 157.77.

EXAMPLE 5

Ethyl 3,5-bis(acetylamino)-2,4,6-triiodobenzoate (WIN 8883)

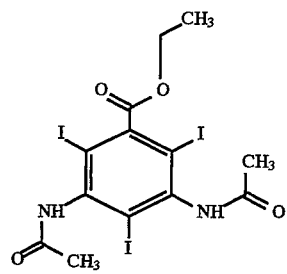

Synthesis of Ethyl 3,5-bis(acetylamino)-2,4,6-triiodobenzoate (WIN 8883)

To 8.11 L of dry N,N-dimethylformamide was added 1.01 kg (1.65 mol) of diatrizoic acid. To the vigorously stirred suspension was carefully added 274 g (1.99 mol) of milled potassium carbonate. During the addition there was significant gas evolution. Before all of the suspended solid had gone into solution, a second solid began to form toward the end of the carbonate addition. The mixture was stirred for 30 min. at room temperature. Ethyl iodide (608 g, 3.90 mmol) was added dropwise and the mixture was stirred overnight at room temperature at which point the reaction mixture was nearly homogeneous. The reaction mixture was poured into 25 L of water, filtered and the solid washed with water and dried at reduced pressure at 60° C. to afford 962 g (91% yield) of a white solid, mp 280°–290° C. (dec.). Analysis for $C_{13}H_{13}I_3N_2O_4$: Calculated: C 24.32, H 2.05, N 4.36. Found C 24.27, H 1.93, N 4.28.

EXAMPLE 6

Bis-[1-(ethoxycarbonyl)propyl]-2,4,6-triiodo-5-acetylamino-isophthalate (WIN 68183)

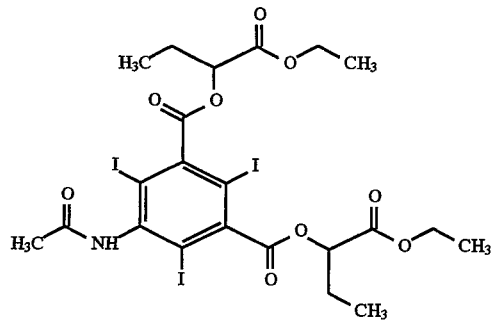

Bis-[1-(ethoxycarbonyl)propyl]-2,4,6-triiodo-5-acetylamino-isophthalate (WIN 68183) was prepared as follows.

Sodium metal (1.9 g, 82.6 mmol) was dissolved in 500 ml of absolute ethanol followed by the addition of 25 g (42 mmol) of 5-substituted-2,4,6-triiodoisophthalic acid. After stirring for 30 minutes the solvent was removed under vacuum to give 36.1 g of the di-sodium salt which was dried under high vacuum and used without further purification.

To a suspension of the sodium salt (10 g, 15.5 mmol) described above in 50 ml of DMF was added ethyl 2-bromobutyrate and the mixture was stirred at ambient temperature for 6 hrs at which point solution was observed. After heating for 1 hr on a steam bath, the solution was cooled and added to a mixture of ice and water. The desired product crystallized from the aqueous solution overnight and was collected by filtration and dried under vacuum to give an essentially quantitative yield of white solid, mp 195°–205° C.; CI-MS: MH⁺830. The ¹H-NMR (300 MHz) spectral data was consistent with the desired material. Calculated for $C_{22}H_{26}I_3NO_9$: C 31.87, H 3.16, I 45.92, N 1.69; Found: C 31.81, H 3.17, I 45.94; N 1.64.

EXAMPLE 7

1,3,5-Triethyl-2,4,6-triiodobenzene (WIN 68756)

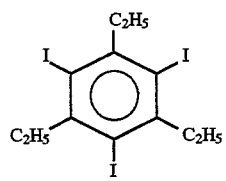

1,3,5-Triethyl-2,4,6-triiodobenzene was prepared in 56% yield from triethylbenzene (5.0 g, 31.4 mmol), [bis (trifluoroacetoxy)iodo]benzene (21.2 g, 49.2 mmol), and iodine (12.5 g, 47.2 mmol) in 50 ml of CCl₄. Recrystallization from cyclohexane gave 9.5 g of pure material. Title Compound: ¹H (300 MHz) and ¹³C (75 MHz) NMR spectra were consistent With the desired product. Calculated for $C_{12}H_{15}I_3$: C 26.69, H 2.80, I 70.51; Found: C 26.84, H 2.54, I 70.39.

EXAMPLE 8

3,5-Bis-acetylamino-2,4,6-triiodo-benzoic acid 4-methoxy-benzyl ester (WIN 67754)

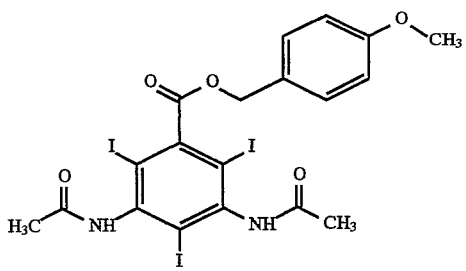

3,5-Bis-acetylamino-2,4,6-triiodo-benzoic acid 4-methoxy-benzyl ester (WIN 67754) was prepared as follows.

To a stirred solution of sodium diatrizoate (25 g, 39 mmol) in 200 ml of DMF was added 4-methoxybenzyl chloride (5.8 ml, 42 mmol) over a 30 minute period. The resulting mixture was stirred overnight at ambient temperature. Additional 4-methoxybenzyl chloride (1 ml) was then added and the mixture was stirred for 24 hrs. The solvent was removed under reduced pressure leaving a white solid residue which was slurried in 300 ml of distilled water. The crude product was collected, washed with water and dried at 70°–75° C. to give a solid which was then digested with 400 ml of chloroform-isopropanol (1:1). Upon cooling, the solid was collected and dried under vaccuum at 80°–85° C. to give the product (24.3 g, 85% yield) as a white granular solid, mp 244°–246° C.; CI-MS: MH⁺735. The ¹H-NMR (300 MHz) spectral data was consistent with the desired product. Calculated for $C_{19}H_{17}I_3N_2O_5$; C 31.09, H 2.33, I 51.86, N 3.82; Found: C 31.05, H 2.23, I 51.84, N 3.84.

EXAMPLE 9

3,5-Bis-acetylamino-2,4,6-triiodo-benzoic acid 4-isopropyl benzoate ester (WIN 67956)

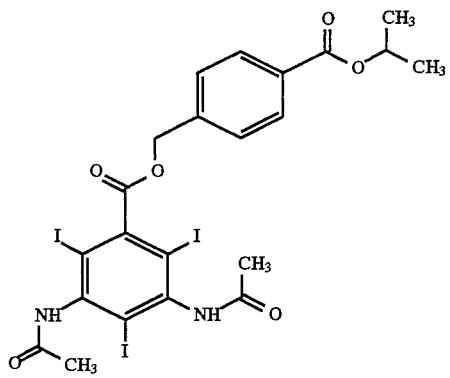

3,5-Bis-acetylamino-2,4,6-triiodo-benzoic acid 4-isopropyl benzoate ester (WIN 67956) was prepared in a manner similar to Example 8.

EXAMPLE 10

6-Ethoxy-6-oxohexyl 3,5-bis(acetylamino)-2,4,6-triiodobenzoate (WIN 67722)

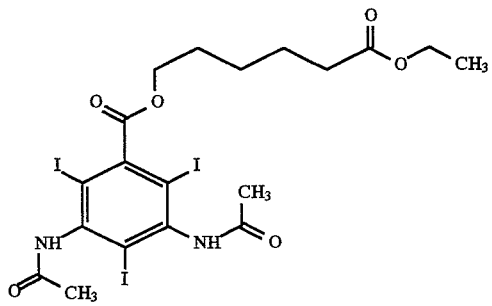

6-Ethoxy-6-oxohexyl 3,5-bis(acetylamino)-2,4,6-triiodobenzoate (WIN 67722) was prepared as follows.

Sodium diatrizoate (16.1 g, 25.3 mmol) was dissolved in 180 ml of dry dimethylformamide and to this solution was added, in one portion, ethyl 6-bromohexanoate (4.5 ml, 25.3 mmol). The reaction mixture was stirred for 12 hrs at ambient temperature and then poured into 1.6 liter of ice-water with stirring. The resulting white precipitate was collected by filtration, dissolved in 1:1 ethanol-ethyl acetate and the solution was treated with magnesium sulfate, decolorizing charcoal and then filtered through a short pad of silica gel. The filtrate was concentrated to dryness and dried to give 16 g (84%) of the desired product. Recrystallization from methanol-water gave analytically pure material, mp 235°–238° C. (decomp. at 275° C.); MS:M⁺756. The ¹H-NMR (300 MHz) spectral data was consistent with the desired product. Calculated for $C_{19}H_{23}I_3N_2O_6$; C 30.18, H 3.07, I 50.35, N 3.70; Found: C 30.26, H 2.88, I 50.40, N 3.65.

EXAMPLE 11

3,5-Bis-acetylamino-2,4,6-triiodo-benzoic acid 5-isopropoxycarbonyl-pentylester (WIN 67995)

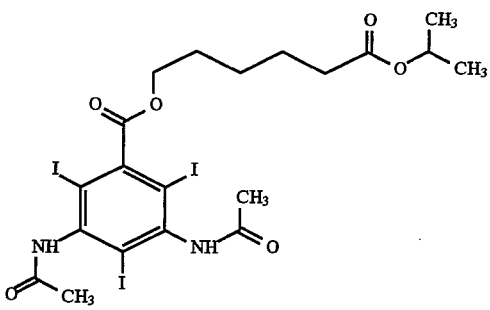

3,5-Bis-acetylamino-2,4,6-triiodo-benzoic acid 5-isopropoxycarbonylpentylester (WIN 67995) was prepared in a manner similar to Example 10.

Method of Preparing the Radiopaque Particulates

The radiopaque particulates were prepared by milling the large radiopaque particles mixed with an appropriate surface active agent to obtain the desired particle size. Alternatively, the large radiopaque particulates may be comminuted to the desired particle size and subsequently intimately mixed with the appropriate surface active agent. The milling technique is described in U.S. Pat. No. 5,145,684, which is incorporated herein by reference.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" for example, it is meant that at least 90% of the particles have a weight average particle size of less than about 400 nm when measured by the above-noted techniques. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm.

The particles of this invention can be prepared in a method comprising the steps of dispersing a radiopaque substance in a liquid dispersion medium and applying mechanical means in the presence of grinding media to reduce the particle size of the radiopaque substance to an effective average particle size of less than about 400 nm. The particles are reduced in size in the presence of the surface active agent. Alternatively, the particles can be intimately mixed with a surface active agent after attrition.

A general procedure for preparing the particles of this invention is set forth below. The radiopaque substance selected is obtained commercially and/or prepared by techniques known in the art in a conventional coarse form. It is preferred, but not essential, that the particle size of the coarse radiopaque substance selected be less than about 100 μm as determined by sieve analysis. If the coarse particle size of the radiopaque substance is greater than about 100 μm, then it is preferred that the particles of the radiopaque substance be reduced in size to less than 100 μm using a conventional milling method such as airjet of fragmentation milling.

The mechanical means applied to reduce the particle size of the radiopaque substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size.

The grinding media for the particle size reduction step can be selected from rigid media preferably spherical or particulate in form having an average size less than about 3 mm and, more preferably, less than about 1 min. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the radiopaque substance. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

Nanosuspension particle size was determined during the milling process and again immediately before the nanosuspensions were administered to rodents. Particle size was determined on the Coulter Model N4MD Submicron Particle Analyzer (Coulter Corp.; Miami Lakes, Fla.); and using the Microtrac Ultrafine Particle Analyzer (Leeds and Northrup Co.; St. Petersburg, Fla.).

The following formulation examples will further illustrate the present invention.

EXAMPLE 12

| | |
|---|---|
| WIN 68183 | 20 g |
| Pluronic F127 | 4.0 g |
| Benzoate Sodium | 0.2 g |
| Saccharin Sodium | 0.1 g |
| FD&C Red No. 40 | 0.03 g |
| Water, qs | 100 ml |

EXAMPLE 13

| WIN 68183 | 15 g |
|---|---|
| Pluronic F127 | 4.0 g |
| Benzoate Sodium | 0.2 g |
| Sorbate Potassium | 0.15 g |
| Saccharin Sodium | 0.1 g |
| FD&C Red No. 40 | 0.03 g |
| Water, qs | 100 ml |

EXAMPLE 14

| WIN 68183 | 25 g |
|---|---|
| Pluronic F88 | 5.0 g |
| Benzoate Sodium | 0.2 g |
| Saccharin Sodium | 0.1 g |
| FD&C Red No. 3 | 0.03 g |
| Water, qs | 100 ml |

EXAMPLE 15

| WIN 8883 | 19 g |
|---|---|
| Sucrose | 10 g |
| Pluronic F77 | 4.0 g |
| Dioctylsulfosuccinate | 0.1 g |
| Methylparabens | 0.2 g |
| Propylparabens | 0.07 g |
| FD&C Yellow No. 5 | 0.03 g |
| Water, qs | 100 ml |

EXAMPLE 16

| WIN 68756 | 15 g |
|---|---|
| Pluronic F127 | 5 g |
| Sorbitol | 5 g |
| Benzoate Sodium | 0.2 g |
| Water, qs | 100 ml |

EXAMPLE 17

| WIN 8883 | 22 g |
|---|---|
| HPMC (2% = 100 cps) | 2 g |
| Steam sterilized by autoclaving at 120° C. for 21 minutes & 5 psig | 0.2 g |
| Water, qs | 100 ml |

EXAMPLE 18

| WIN 67754 | 20 g |
|---|---|
| Pluronic F127 | 4.0 g |
| Benzoate Sodium | 0.2 g |
| Sorbate Potassium | 0.15 g |
| Saccharin Sodium | 0.1 g |
| Water, qs | 100 ml |
| Hydrochloric Acid | adjust to pH 4.0 |

Determining Imaging Efficacy

X-ray diagnostic imaging was performed in anesthetized rats with the exception of G05-R1 samples which were imaged in fasted and anesthetized ferrets. Images were obtained using the Siemens C-Arm Siremobil 3U x-ray unit. The imaging dose was 10 ml/kg administered via gastric intubation to the anesthetized animal. X-rays were taken at 15, 30, 45 and 60 minutes and at 1, 2, 5 and 24 hours post-dose. A 10–15 ml volume of air was introduced to the animal at 30 minutes to produce a double contrast image.

Images were evaluated by the criteria of coating, homogeneity, rate of gastric emptying and the total transit time. These are considered to be a measure of the stability of the nanosuspension during transit down the GI tract and the ability of the formulation to image the lower gastrointestinal tract. Nanosuspensions were rated excellent when there was a uniform coating with transradiation of long intestinal segments, sufficient radiodensity to delineate anatomical structure, rapid emptying and transit, and stability and homogeneity during GI transit. A plus sign (+) was assigned when imaging in the lower GI was exceptional, a minus sign (−) as given when it was not. The nanosuspension of WIN 8883 milled in Pluronic F127, was considered to be excellent for both upper and lower GI imaging in both rats and ferrets. All other nanosuspensions were compared with this formulation.

The various polymeric surfactants and additional excipients used to prepare nanosuspensions are listed in Table 2. Nanosuspensions of WIN 8883 were milled at 20% weight per volume in presence of 4% w/v solutions of stabilizers unless specified otherwise.

TABLE 2

Surfactants Used for the Preparation of Nanoparticulate Formulations

| SURFACTANT | GRADE | SOURCE |
|---|---|---|
| PLURONIC F127 | NF | BASF |
| PLURONIC F68 | NF | BASF |
| PLURONIC F77 | NF | BASF |
| PLURONIC F87 | NF | BASF |
| PLURONIC F88 | NF | BASF |
| PLURONIC F98 | NF | BASF |
| PLURONIC F108 | NF | BASF |
| TETRONIC T908 | PRILL (RM) | BASF |
| TYLOXAPOL | RM | SIGMA |
| POLYVINYL ALCOHOL Avg. MW 30–70K | RM | SIGMA |
| POLYVINYL PYRROLIDONE (PVP 40) MW 40K | RM | SIGMA |
| HYDROXYPROPYLMETHYL CELLULOSE (HPMC: 2% SOLUTION = 100 CPS) | RM | SIGMA |
| POLYOXYETHYLENE SORBITAN MONO-OLEATE (TWEEN 80) | RM | SIGMA |
| DIOCTYLSULFOSUCCINATE, DOSS | RM | SIGMA |

RM = Commercial Grade Raw Material
NF = National Formulary

The efficacy of the nanoparticulate formulations to image the GI tract is shown in Table 3. Overall, compounds with the lowest aqueous solubility were often the most efficacious. WIN 68183 and WIN 68756 were considered to be excellent imaging agents as compared with WIN 8883, however, lower GI imaging was not as definitive as with WIN 8883. WIN 67754 was scored as good overall and exhibited exceptional lower GI imaging. Initially WIN 67956 showed very rapid gastric emptying and therefore was repeated with air given at 15 minutes to induce double contrast. No improvement in coating was seen with this compound and it was rated as good. WIN 67722 and WIN 67995 were rated as good in the upper GI, however, imaging efficacy in the lower GI was poor. WIN 59316, WIN 68165 and WIN 67975 were rated as fair, with only WIN 59316 imaging well in the lower GI tract.

TABLE 3

Imaging Efficacy of Nanoparticulate Formulations Prepared with Pluronic F127

| Code | WIN No. | Aqueous Solubility (μg/ml) | Days Milled | Milling Process(a) | Particle Size (nm)(b) | Range(c) | Imaging Efficacy(d,e) |
|---|---|---|---|---|---|---|---|
| G05 | 8883 | <5 | 1.8 | P | 186/ND | Narrow | ++++(*) |
| G05 R2 | 8883 | <5 | 5 | JM | 135/ND | 80–230 | ++++(*) |
| G09 | 68183 | <1 | 9 | JM | 139/ND | 95–169 | ++++(*) |
| G10 | 68756 | <1 | <1 | P3R | 165/154 | 94–395 | ++++ |
| G06 | 67754 | 15 | 9 | JM | 152/ND | 95–300 | +++(*) |
| G08 | 67956 | 1 | 14 | JM | 221/ND | 125–478 | +++ |
| G08 R1 | 67956 | 1 | 7 | JM | 241/223 | 130–686 | +++ |
| G11 | 67722 | 2 | <1 | P3R | 150/146 | 84–442 | +++(−) |
| G16 | 67995 | 1 | 4 | JM | 156/171 | 97–253 | +++(−) |
| G07 | 59316 | 1 | 14 | JM | 678/ND | 185–900 | ++(*) |
| G12 | 67975 | 8 | <1 | P3R | 211/206 | 93–910 | ++(−) |
| G13 | 68165 | 1 | <1 | P6R | 742/1060 | 527–1704 | ++ |

(a)P = Planetary Mill, JM = Jar Mill, P(N)R = 18 hour planetary mill and N = number of days Jar Mill.
(b)Post-milling/pre-dose particle size; ND = Not Determined.
(c)Range(nm) = Size Distribution for 10 to 99% of the particles by weight.
(d)Imaging efficacy is indicated as follows:
Excellent++++ Good+++ Fair++ Poor+
(e)Formulations with efficacy followed by (*) signs indicate exceptional lower GI imaging while those with (−) sign were found to be unacceptable in the lower GI.

Efficacy of Nanoparticulate Formulations Prepared with Alternate Surfactants as X-Ray Contrast Agent The imaging efficacy of nanosuspension formulations with alternate surfactants are shown in Table 4.

Excellent imaging was obtained from nanosuspensions of WIN 8883 stabilized with Pluronic F77 with 0.1% DOSS added (G29) and with Pluronic F88 (G04), however, these nanosuspensions did not image the lower GI as effectively as G05.

Good imaging was obtained from nanosuspensions of WIN 8883 stabilized with polyvinyl alcohol (PVA) (G21), tyloxapol (G20), tyloxapol with 0.1% w/v DOSS (G37), hydroxypropyl methylcellulose (G22), F88 with 0.1% DOSS (G27), and F87 (G26). Good upper GI imaging was obtained from nanosuspensions of WIN 8883 stabilized with F98 (G14), F108 (G15) and F68 with 0.1% w/v DOSS (G23). Fair imaging was obtained from the WIN 8883 nanosuspensions stabilized with T908 (G01), Tween 80 (G3), 1% w/v DOSS (G18), polyvinyl pyrrolidone, (PVP 40) (G19) and F87 with 1% w/v DOSS (G25). Poor imagining was obtained when no stabilizer was used (G02) and the formulation with F77 alone (G28) gelled during milling and therefore was not imaged. Nanosuspension G18, prepared in 1.0% w/v DOSS was foamy, and G19, 4% PVP 40 milled to a thick foam.

DOSS and HPMC were found to be fair in regard to their stabilizing effect on imaging efficacy. DOSS itself was found to be fair (G18) while HPMC was rated as good, even with particle sizes greater than 700 rim. DOSS was needed to stabilize the nanosuspension prepared in 4% w/v Pluronic F77 (G29). The same formulation without DOSS could not be imaged due to gelling during the milling process.

DOSS had variable effects when used in conjunction with other stabilizers. The nanosuspension stabilized with F88 (G04) was rated as excellent. When 0.1% w/v DOSS was used as a secondary stabilizer (G24), the imaging efficacy was rated only as good. A similar result was noted with nanosuspensions stabilized with F87. The suspension without DOSS (G26) was rated higher in imaging efficacy than did the same suspension with 0.1% w/v DOSS (G25). Nanosuspensions stabilized with 4% w/v tyloxapol plus 0.1% w/v DOSS (G27) or without DOSS (G20) were both rated good. Milling time, however, was reduced and overall particle size was smaller with the DOSS-added suspension.

TABLE 4

Imaging Efficacy of Diagnostic Agents Prepared with Alternative Surfactants

| I.D. | Stabilizer (w/v) | Days Milled | Milling Process | Particle Size (nm)(b) | Range(c) | Imaging Efficacy(d,e,f) |
|---|---|---|---|---|---|---|
| G02 | None | 6 | JM | 1000/ND | Broad | + |
| G05 | 4% F127 | 1.8 | P | 186/ND | Narrow | ++++(*) |
| G29 | 4% F77/ 0.1% DOSS | 5 | JM | 146/187 | 66–243 | ++++ |
| EG04 | 4% F88 | 1.8 | P | 183/ND | Narrow | +++(−) |
| G21 | 4% PVA | 6 | JM | 204/199 | 134–405 | +++(*) |
| G26 | 4% F87 | 5 | JM | 155 | 55–265 | +++ |
| G20 | 4% Tyloxapol | 6 | JM | 180/262 | 137–521 | +++ |
| G22(f) | 2% HPMC | 6 | JM | 334/700 | 350–2596 | +++ |
| G24 | 4% F88/ 0.1% DOSS | 5 | JM | 160 | 146–265 | +++ |
| G27 | 4% Tyloxapol/ 0.1% DOSS | 5 | JM | 140 | 66–315 | +++ |
| G23 | 5% F68/ 0.1% DOSS | 4 | JM | 147/170 | 108–602 | +++(−) |
| G03 | 4% Tween 80 | 6 | JM | 161/ND | Narrow | ++ |
| G18(f) | 1% DOSS | 4 | JM | 119/130 | 85–247 | ++ |
| G19(f) | 4% PVP | 5 | JM | 673/823 | 620–1265 | ++ |
| G25 | 4% F87/ | 5 | JM | 150 | 66–243 | ++ |

TABLE 4-continued

Imaging Efficacy of Diagnostic Agents Prepared with Alternative Surfactants

| I.D. | Stabilizer (w/v) | Days Milled | Milling Process | Particle Size (nm)[b] | Range[c] | Imaging Efficacy[d,e,f] |
|---|---|---|---|---|---|---|
| | 0.1% DOSS | | | | | |

[a]P = Planetary Mill, JM = Jar Mill, P(N)R = 18 hour planetary mill and N = number of days Jar Mill
[b]Post-milling/pre-dose particle size; ND = Not Determined. Formulations G24 through G28, G30 and G32 were sized within 24 hours of milling; others were sized when the milling was terminated.
[c]Range(nm) = Size Distribution for 10 to 99% of the particles by weight.
[d]Imaging efficacy is indicated as follows:
Excellent++++ Good+++ Fair++ P+
[e]Formulations with efficacy followed by (*) signs indicate exceptional lower GI imaging while those with (−) signs were found to be unacceptable in the lower GI.
[f]Foaming was evident in G18 (1% DOSS), very thick foam was found in G19 (4% PVP) and in G22 (2% HPMC).

Comparison of Pluronic F127 vs. F88 Surfactants

The two alternate compounds stabilized with Pluronic F127 and which demonstrated excellent imaging efficacy in the rat (WIN 68183 and WIN 68756), were subsequently milled with F88 with a resultant loss of efficacy as shown in Table 5.

TABLE 5

Comparison of Efficacy Between Pluronic F88 and Pluronic F127

| I.D. | WIN No | Pluronic | Days Milled | Milling Process[a] | Particle Size (nm)[b] | Range[c] | Imaging Efficacy[d,e,f] |
|---|---|---|---|---|---|---|---|
| G05 | 8883 | F127 | 1.8 | P | 186/ND | Narrow | ++++(*) |
| G09 | 68183 | F127 | 9 | JM | 139/ND | 95–169 | ++++ |
| G010 | 68756 | F127 | P3R | — | 165/154 | 94–395 | ++++ |
| G04 | 8883 | F88 | 1.8 | P | 183/ND | Narrow | ++++(−) |
| G31 | 68756 | F88 | 3 | JM | 209 | 118–578 | +++ |
| G17 | 68183 | F88 | 8 | JM | 146/125 | 77–237 | +++(−) |

[a]P = Planetary Mill, JM = Jar Mill, P(N)R = 18 hour planetary mill and N = number of days Jar Mill
[b]Post-milling/pre-dose particle size; ND = Not Determined.
[c]Range(nm) = Size Distribution for 10 to 99% of the particles by weight (pre-image where indicated)
[d]Imaging efficacy is indicated as follows:
Excellent++++ Good+++ Fair++ P+
[e]Formulations with efficacy followed by (*) signs indicate exceptional lower GI imaging while those with (−) signs were found to be unacceptable in the lower GI.
[f]G31 was imaged within 24 hours of milling.

Summarizing the above-described test results, twenty different stabilizers were examined using nanosuspensions of WIN 8883, of these, Pluronic F127 was considered excellent for imaging both the upper and lower GI. A nanosuspension stabilized with F88 was judged as excellent but for the upper GI only. Twenty compounds gave acceptable results as oral GI x-ray imaging agents. Three compounds (WIN 8883, WIN 68183 and WIN 68756) and one stabilizer, Pluronic F127, was recognized as an excellent oral GI x-ray imaging agent. When nanosuspensions of these same three compounds were stabilized with F88, only the WIN 8883 nanosuspension produced excellent imaging, and then only in the upper GI.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orally/rectally administrable gastrointestinal diagnostic x-ray contrast formulation comprising:

a—of from about 4 to about 45% w/v of an essentially water-insoluble particulate radiopaque crystalline material having an effective average particle size of less than about 2,000 nm;

b—of from about 0.1 to about 10% w/v of a bioadhesive surfactant stabilizer selected form the group consisting of:

(i) polyethylene-polypropylene glycol block polymers of the formula

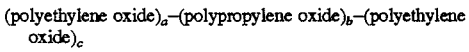

(polyethylene oxide)$_a$–(polypropylene oxide)$_b$–(polyethylene oxide)$_c$ wherein
   a is 46 to 128;
   b is 16 to 67; and
   c is 46 to 128; and
   c—water to make 100% w/v.

2. The orally/rectally administrable gastrointestinal diagnostic x-ray contrast formulation of claim 1 wherein said particulate radiopaque crystalline material is selected from the group consisting of: 3,5-Bis-acetylamino-2,4,6-triiodobenzoic acid ethyl ester (WIN 05316), 2-(3,5-Bis-acetylamino-2,4,6-triiodo-benzyloxy)-2-methyl malonic acid (WIN 67975), Propanedioic Acid, [[3,5-bis-(acetylamino)-2,4,6-triiodo-benzoyl]oxy]-bis(1-methylethyl) ester acid ethyl ester (WIN 68165), Diethyl 5-acetylamino-2,4,6-triiodo-isophthalate (WIN 59316), Ethyl 3,5-bis(acetylamino)-2,4,6-triiodobenzoate (WIN 8883), Bis-[1-(ethoxycarbonyl)propyl]-2,4,6-triiodo-5-acetylamino-isophthalate (WIN 8183), 1,3,5-Triethyl-2,4,6-triiodobenzene (WIN 68756), 3,5-Bis-acetylamino-2,4,6-triiodo-benzoic acid 4-methoxy-benzyl ester (WIN 67754), 3,5-Bis-acetylamino-2,4,6-triiodo-benzoic acid 4-isopropyl benzoate ester (WIN 67956), (6-Ethoxy-6-oxohexyl 3,5-bis(acetylamino)-2,4,6-triiodobenzoate) (WIN 67722) and 3,5-Bis-acetylamino-2,4,6-triiodo-benzoic acid 5-isopropoxycarbonylpentylester (WIN 67995).

3. The orally/rectally administrable gastrointestinal diagnostic x-ray contrast formulation of claim 1 wherein said particulate radiopaque crystalline material is selected from the group consisting of: barium sulfate, barium hexaborite, barium chromite, barium fluogallate, barium tri-ortho phosphate, barium metasilicate, barium titanate and barium zirconate.

4. The orally/rectally administrable gastrointestinal diagnostic x-ray contrast formulation of claim 1 further comprising up to 1% w/v of a secondary stabilizer selected from the group consisting of dioctylsulfosuccinate and sodium lauryl sulfate.

5. A method of carrying out x-ray examination of the gastrointestinal tract of a patient, said method comprises the oral/rectal administration to the patient an x-ray contrast composition comprising:

a—of from about 4 to about 45% w/v of an essentially water-insoluble particulate radiopaque crystalline material having an effective average particle size of less than about 2,000 nm;

b—of from about 0.1 to about 10% w/v of a bioadhesive surfactant stabilizer selected form the group consisting of:

(i) polyethylene-polypropylene glycol block polymers of the formula (polyethylene oxide)$_a$–(polypropylene oxide)$_b$–(polyethylene oxide)$_c$ wherein
a is 46 to 128;
b is 16 to 67; and
c is 46 to 128; and
c—water to make 100% w/v.

6. The method of claim 5 wherein said particulate radiopaque crystalline material is selected from the group consisting of: 3,5-Bis-acetylamino-2,4,6-triiodo-benzoic acid ethyl ester (WIN 05316), 2-(3,5-Bis-acetylamino-2,4,6-triiodo-benzyloxy)-2-methyl malonic acid (WIN 67975), Propanedioic Acid, [[3,5-bis-(acetylamino)-2,4,6-triiodo-benzoyl]oxy]-bis(1-methylethyl) ester acid ethyl ester (WIN 68165), Diethyl 5-acetylamino-2,4,6-triiodo-isophthalate (WIN 59316), Ethyl 3,5-bis(acetylamino)-2,4,6-triiodobenzoate (WIN 8883), Bis-[1-(ethoxycarbonyl)propyl]-2,4,6-triiodo-5-acetylamino-isophthalate (WIN 68183), 1,3,5-Triethyl-2,4,6-triiodobenzene (WIN 68756), 3,5-Bis-acetylamino-2,4,6-triiodo-benzoic acid 4-methoxy-benzyl ester (WIN 67754), 3,5-Bis-acetylamino-2,4,6-triiodo-benzoic acid 4-isopropyl benzoate ester (WIN 67956), (6-Ethoxy-6-oxohexyl 3,5-bis(acetylamino)-2,4,6-triiodobenzoate) (WIN 67722) and 3,5,-Bis-acetylamino-2,4,6-triiodo-benzoic acid 5-isopropoxycarbonylpentylester (WIN 67995).

7. The method of claim 5 wherein said particulate radiopaque crystalline material is selected from the group consisting of: barium sulfate, barium hexaborite, barium chromite, barium fluogallate, barium tri-ortho phosphate, barium metasilicate, barium titanate and barium zirconate.

8. The method of claim 5 wherein said composition further comprises up to 1% w/v of a secondary stabilizer selected from the group consisting of dioctylsulfosuccinate and sodium lauryl sulfate.

9. The orally/rectally administrable gastrointestinal diagnostic x-ray contrast formulation of claim 1 comprising:

a—of from about 5 to about 25% w/v of an essentially water-insoluble particulate radiopaque crystalline material having an effective average particle size of less than about 400 nm;

b—of from about 1 to about 6% w/v of a bioadhesive surfactant stabilizer being:

(i) polyethylene-polypropylene glycol block polymers of the formula (polyethylene oxide)$_a$–(polypropylene oxide)$_b$–(polyethylene oxide)$_c$ wherein
a, b and c are 98, 67 and 98 respectively or 122, 47 and 122 respectively; and c—water to make 100% w/v.

10. The method of claim 5, said method comprising the oral/rectal administration to the patient an x-ray contrast composition comprising:

a—of from about 5 to about 25% w/v of an essentially water-insoluble particulate radiopaque crystalline material having an effective average particle size of less than about 400 nm;

b—of from about 1 to about 6% w/v of a bioadhesive surfactant stabilizer being:

(i) polyethylene-polypropylene glycol block polymers of the formula (polyethylene oxide)$_a$–(polypropylene oxide)$_b$–(polyethylene oxide)$_c$ wherein
a, b and c are 98, 67 and 98 respectively or 122, 47 and 122 respectively; and c—water to make 100% w/v.

* * * * *